United States Patent
Yamamoto (10) Patent No.: US 8,890,517 B2
(45) Date of Patent: Nov. 18, 2014

(54) EDDY CURRENT MEASURING SENSOR

(75) Inventor: Takanari Yamamoto, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 93 days.

(21) Appl. No.: 13/641,207

(22) PCT Filed: Jan. 21, 2011

(86) PCT No.: PCT/JP2011/051067
§ 371 (c)(1),
(2), (4) Date: Oct. 15, 2012

(87) PCT Pub. No.: WO2011/135872
PCT Pub. Date: Nov. 3, 2011

(65) Prior Publication Data
US 2013/0038322 A1    Feb. 14, 2013

(30) Foreign Application Priority Data
Apr. 27, 2010   (JP) ................. 2010-102751

(51) Int. Cl.
*G01N 27/90*   (2006.01)
*G01N 27/80*   (2006.01)

(52) U.S. Cl.
CPC ..................... *G01N 27/80* (2013.01)
USPC ......................... 324/240; 324/242

(58) Field of Classification Search
CPC .............. G01N 27/72; G01N 27/82
USPC .................................. 324/240, 242
See application file for complete search history.

(56) References Cited

U.S. PATENT DOCUMENTS 6,822,429 B2   11/2004   Golder et al.

FOREIGN PATENT DOCUMENTS

| JP | U-05-043066 | 6/1993 |
| JP | U-5-43066 | 6/1993 |
| JP | A-2003-185758 | 7/2003 |
| JP | A-2006-010440 | 1/2006 |
| JP | A-2007-040865 | 2/2007 |
| JP | A-2008-185436 | 8/2008 |
| JP | A-2009-002681 | 1/2009 |
| JP | A-2009-236679 | 10/2009 |

OTHER PUBLICATIONS

Yamamoto et al., "Development of Hardening Depth Evaluation Technique using Eddy Current—Establishment and Introduction of In-line Hardening Depth Inspection System," *SAE World Congress*, *SAE Paper*, 2009-01-0867, 2009, 7 pages.

*Primary Examiner* — Reena Aurora
(74) *Attorney, Agent, or Firm* — Oliff PLC

(57) ABSTRACT

An eddy current measuring sensor including a probe which is configured as a regular triangle and is provided with an excitation unit for applying a given AC excitation signal to a workpiece and a detection unit for detecting a detection signal occurring in an object to be measured responsive to the applied AC excitation signal, wherein the excitation unit is provided with exciting coils which are arranged on each side of the probe, while the detection unit is provided with detection coils which are arranged at each vertex of the probe.

6 Claims, 11 Drawing Sheets

EDDY CURRENT MEASURING SENSOR

TECHNICAL FIELD

The present invention relates to a sensor for measuring eddy currents, and particularly to a technique of improving accuracy thereof.

BACKGROUND ART

For machine parts such as engine parts and underbody parts of automobiles or motorcycles, steel materials are used, to which the induction hardening is performed, namely the metal (conductive material) to which high-frequency induction heating is performed. As to the high-frequency hardening to the steel material, case depth after hardening by the surface hardening (hereinafter called "hardening depth") and hardness are standardized in effective case depth after hardening and total case depth after hardening. Thus, in order to guarantee quality of the steel material, the hardening depth and the hardness are required to be measured and evaluated.

The hardening depth and the hardness of the steel material are conventionally evaluated by measurement with Vickers hardness tester or the like, which measures the strength of a cross section of a steel material as a sample.

Due to the destructive inspection, the steel material as the sample is wasted and therefore the material cost rises. Moreover, it takes long time to inspect and the total inspection in the in-line inspection would be impossible, and the defects accidentally occurred are not detected and the product with defects may be transferred to the next process.

There are some techniques using eddy current inspection (measurement) as a non-destructive inspection to measure the hardening depth and the hardness of the steel material (e.g., Patent Literatures 1 to 6 and Non-Patent Literature 1).

The eddy current inspection is to generate an alternating magnetic field by putting an exciting coil with alternating currents close to the steel material, generating eddy currents in the steel material caused by the alternating magnetic field, and to detect an induction magnetic field induced by the eddy currents with a detection coil. The eddy current inspection makes it possible to prevent waste and to measure the hardening depth and hardness of the steel material in total inspection in a short time.

Such eddy current inspection is used not only for measuring the hardening depth and hardness of the steel material (hereinafter called "hardening depth inspection") but also for detecting flaws such as cracks on the surface of the object or detecting foreign matters contained in the object.

In the steel material, there occurs the difference in electric conductivity between the base layer and the hardened layer (martensitic layer). Therefore, when measuring the steel material with the eddy current sensor, the voltage, or the amplitude, detected by the detection coil differs in accordance with the change of the hardening depth. Furthermore, the voltage monotonically decreases in accordance with increase of the hardening depth. The hardening depth inspection uses such phenomenon to calculate the hardening depth of the steel material.

For instance, JP 2009-236679 A (PTL1) uses an annular coil to detect the hardening depth of axis of a shaft member. The annular coil can generate the stronger magnetic field than a probe coil that measures the hardening depth with a coil perpendicular to the steel material, and the distance between the annular coil and the steel material may not be strictly controlled, so that the annular coil is useful for the hardening depth inspection.

The steel material must be inserted into the annular coil, and the object is limited to the shaft member having the constant outer diameter. In other words, the annular coil cannot be applicable to the steel material having the complicated inside shape in which the hardening is performed three-dimensionally such as an outer race for a constant velocity joint ("CVJ outer race").

JP 2007-40865 A (PTL2) discloses the technique of measuring the hardening depth with the probe coil.

JP 2006-10440 A (PTL3) discloses the magnetic sensor having multiple coils in which the intervals between the coils are not constant.

JP 2008-185436 A (PTL4) discloses the device for identifying a characteristic of a metal member including four detection coils and an exciting coil.

JP 2009-2681 A (PTL5) discloses the device for measuring the magnetic in which the detection coil is movable.

JP 2003-185758 A (PTL6) discloses the sensor including three detection coils.

NPTL 1 discloses the technique of introduction for mass production of in-line inspection for hardening depth using the eddy current inspection.

As to the hardening depth inspection, the rate of detection signal with respect to that of noise is smaller than the other inspections, so that the hardening depth inspection needs higher detection accuracy. In the case where the object is the steel material such as the CVJ outer race having the complex inside shape in which the hardening is performed three-dimensionally, stability and repeatability are required in positioning the probes, and therefore it is difficult to utilize the eddy current inspection.

[Patent Literature 1] JP 2009-236679 A
[Patent Literature 2] JP 2007-40865 A
[Patent Literature 3] JP 2006-10440 A
[Patent Literature 4] JP 2008-185436 A
[Patent Literature 5] JP 2009-2681 A
[Patent Literature 6] JP 2003-185758 A
[Non-Patent Literature 1] Takanari Yamamoto and Tetsuya Yamaguchi "Development of Hardening Depth Evaluation Technique using Eddy Current-Establishment and Introduction of In-line Hardening Depth Inspection System-", SAE World Congress, SAE Paper 2009-01-0867, 2009

SUMMARY OF INVENTION

Technical Problem

The invention aims to provide an eddy current measuring sensor enabled to secure the stability and repeatability in positioning the probes, even if the object is the steel material such as the CVJ outer race having the complicated inside shape in which the hardening is performed three-dimensionally.

Technical Solutions

The following are expressions to solve the technical problems.

The first embodiment of the invention is an eddy current measuring sensor that includes a probe configured in regular polygon, and the probe comprising an excitation unit for applying a predetermined alternating current excitation signal to an object to be measured and a detection unit for detecting a detection signal generated in the object in response to the alternating current excitation signal. The excitation unit includes multiple exciting coils arranged along the each side of the probe, and the detection unit includes multiple detection coils arranged at the each vertex of the probe. Locating the probe in the proximity of the object, an alternating voltage as the excitation signal is applied to at least one of the exciting coils, whereby a magnetic field is produced at a portion of the object facing the detection coil and an eddy current is generated by the magnetic field, and an inductive voltage generated by the eddy current is detected as the detection signal by means of at least one of the detection coils, whereby the eddy current measuring is performed on the basis of the detection signal. In the advantageous embodiment, the detection unit further includes a balance coil arranged at the center of the probe for cancelling the electromotive forces generated by the detection coils each other.

More preferably, the detection coil is configured to be extendable outward from the vertex of the probe.

In the preferable embodiment, the detection coil is arranged via an elastic member, whereby the detection coil is extendable outward.

In the alternative embodiment, the detection unit further includes a second detection coil arranged at least one side of the probe and outer than the exciting coil. Locating the probe in the proximity of the object, an alternating voltage as the excitation signal is applied to at least one of the exciting coils, whereby a magnetic field is produced at a portion of the object facing the second detection coil and an eddy current is generated by the magnetic field, and an inductive voltage generated by the eddy current is detected as the detection signal by means of the second detection coil, whereby the eddy current measuring is performed on the basis of the detection signal.

Advantageous Effects of Invention

Advantageous effects of the invention are described below.

According to the invention, in the case that the object is the steel material having the complex inside shape to which the hardening is performed three-dimensionally, the positioning of the probe can be provided with high stability and repeatability, and the eddy current inspection can be utilized.

DESCRIPTION OF EMBODIMENTS

Embodiments are described below.

It should be noted that the scope of the invention is not limited to the embodiments, but broadly contains the whole technical idea that is described in the description and the drawings.

The invention aims to improve the applicable scope of the eddy current measurement by means of configuring both of an excitation unit and a detection unit as multiple coils and innovating the arrangement or connection thereof. In the below description, embodiments according to the invention are described. In the embodiments, an eddy current measuring sensor is used for inspection of the hardening quality (hardening depth and hardness) of the object quenched by a high-frequency hardening. The eddy current measurement using the eddy current measuring sensor is performed to inspect the hardening quality of the object.

The eddy current measuring sensor in accordance with the invention can be used not only for the hardening depth inspection but also for detecting flaws or foreign matters contained in the workpiece.

Figure 1:
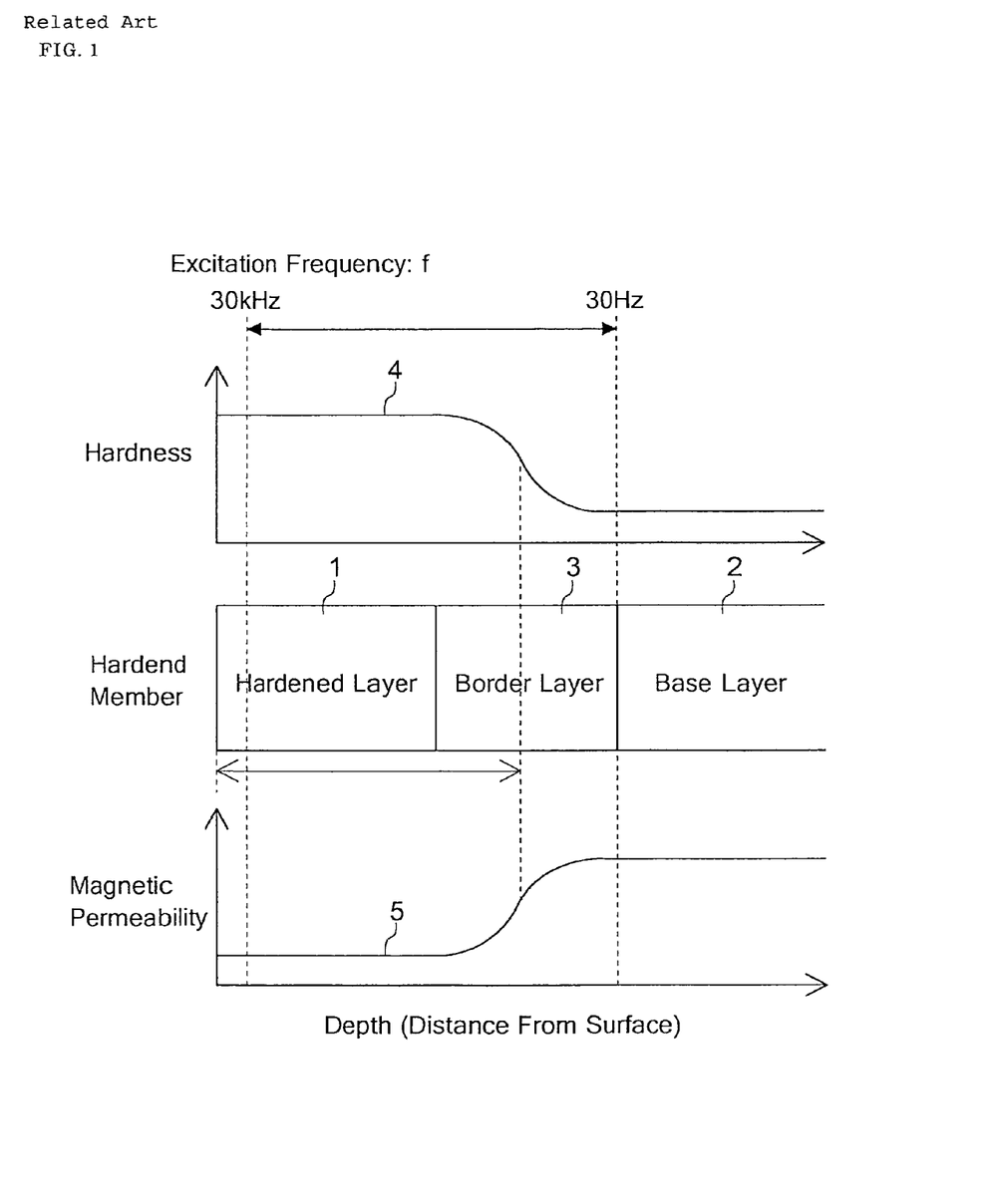
FIG. 1 shows a relationship between the layer state in accordance with the depth, the hardness and the magnetic permeability in a hardened member.

FIG. 1 shows the relationship among the hardness, the magnetic permeability and the layer states corresponding to the depth direction (distance from the surface) of the hardened member, or the hardened steel material (S45C or the like). As shown in FIG. 1, the hardened member is formed with a hardened layer 1 and a base layer 2 between which a border layer 3 is interposed. Referring to the hardness curve 4, the hardness of the hardened layer 1 is larger than that of the base layer 2. As to the border layer 3, the hardness gradually decreases from the hardened layer 1 to the base layer 2. The Vickers hardness of the hardened layer 1 is, for example, 600 to 700 [Hv], and that of the base layer 2 is approximately 300 [Hv].

Referring to the magnetic permeability curve 5, the change of the permeability along the distance from the surface of the hardened member is in inverse proportion to the change of the hardness. The permeability of the hardened layer 1 is smaller than that of the base layer 2, and that of the border layer 3 gradually increases from the hardened layer 1 to the base layer 2. In the embodiment, the eddy current inspection uses the relationship between the hardness and the permeability with respect to the distance from the surface of the hardened member.

Figure 2:
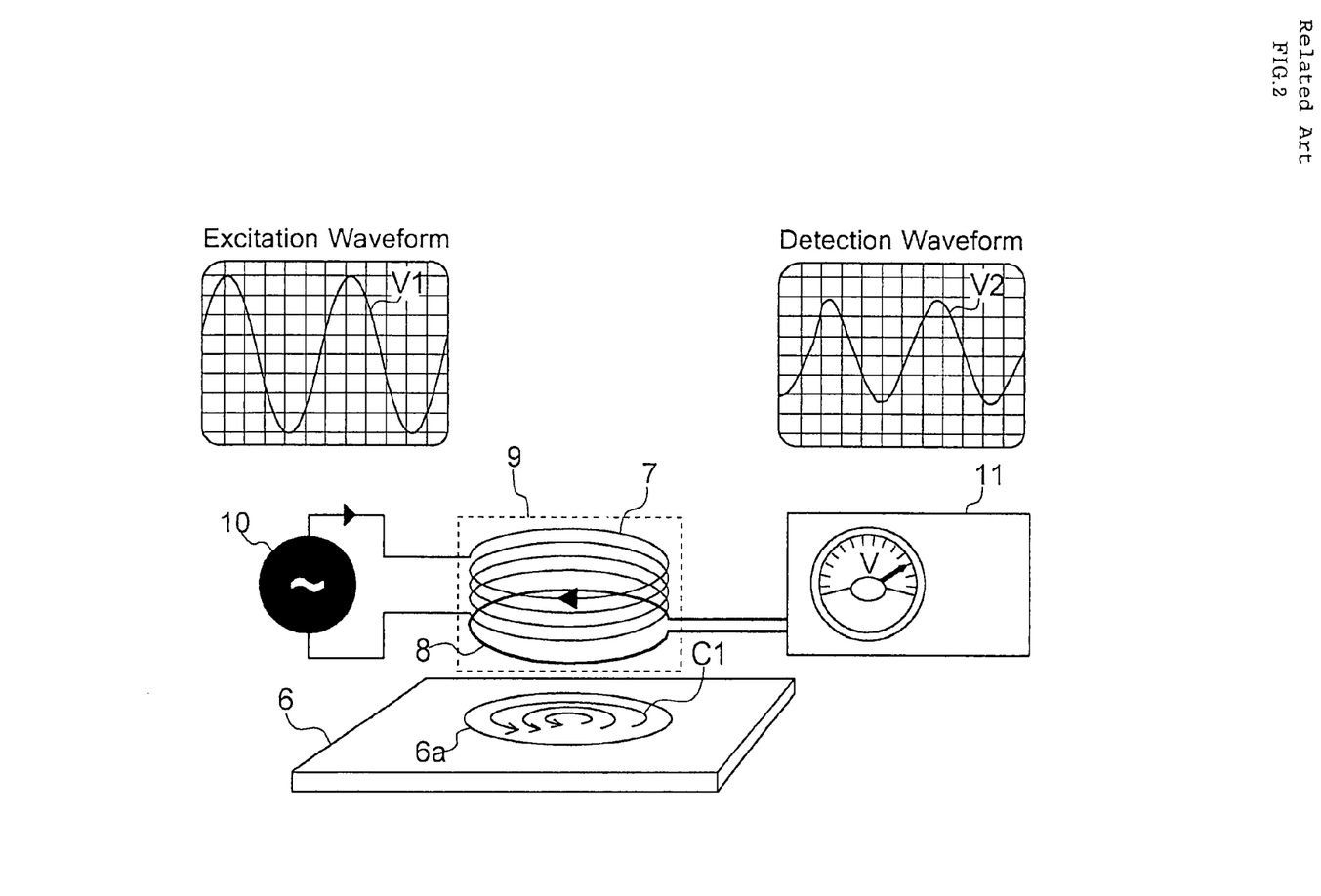
FIG. 2 depicts a structure for inspecting eddy currents.

FIG. 2 depicts the schematic structure (measurement principle) for measuring the eddy current. As depicted in FIG. 2, a workpiece (magnetic body) 6 as the inspection object has a portion to be measured 6a, to which an eddy current measuring sensor 9 including an exciting coil 7 and a detection coil 8 is set in the predetermined position. A current flow in the exciting coil 7 causes the magnetic field around the coil 7. A magnetic induction causes an eddy current in the proximity of the surface of the portion 6a of the magnetic body 6 (see Arrow C1 in FIG. 2). With the eddy current in the surface of the portion 6a, the magnetic flux penetrates the detection coil 8, and the inductive voltage occurs in the detection coil 8. Thus, the detection coil 8 can measure the inductive voltage.

The exciting coil 7 is connected to an alternating current source 10. The AC source 10 applies an alternating current excitation signal V1 to the exciting coil 7. The detection coil 8 is connected to a measurement device 11. The measurement device 11 detects the amplitude of a detection signal V2 detected by the detection coil 8 when the AC excitation signal V1 is applied to the excitation coil 7 and a phase difference (I) of the detection signal V2 with respect to the AC excitation signal V1 (see FIG. 3). The measurement device 11 is provided with the AC excitation signal V1 (waveform) as an amplified detection to detect the phase difference Φ.

Figure 3:
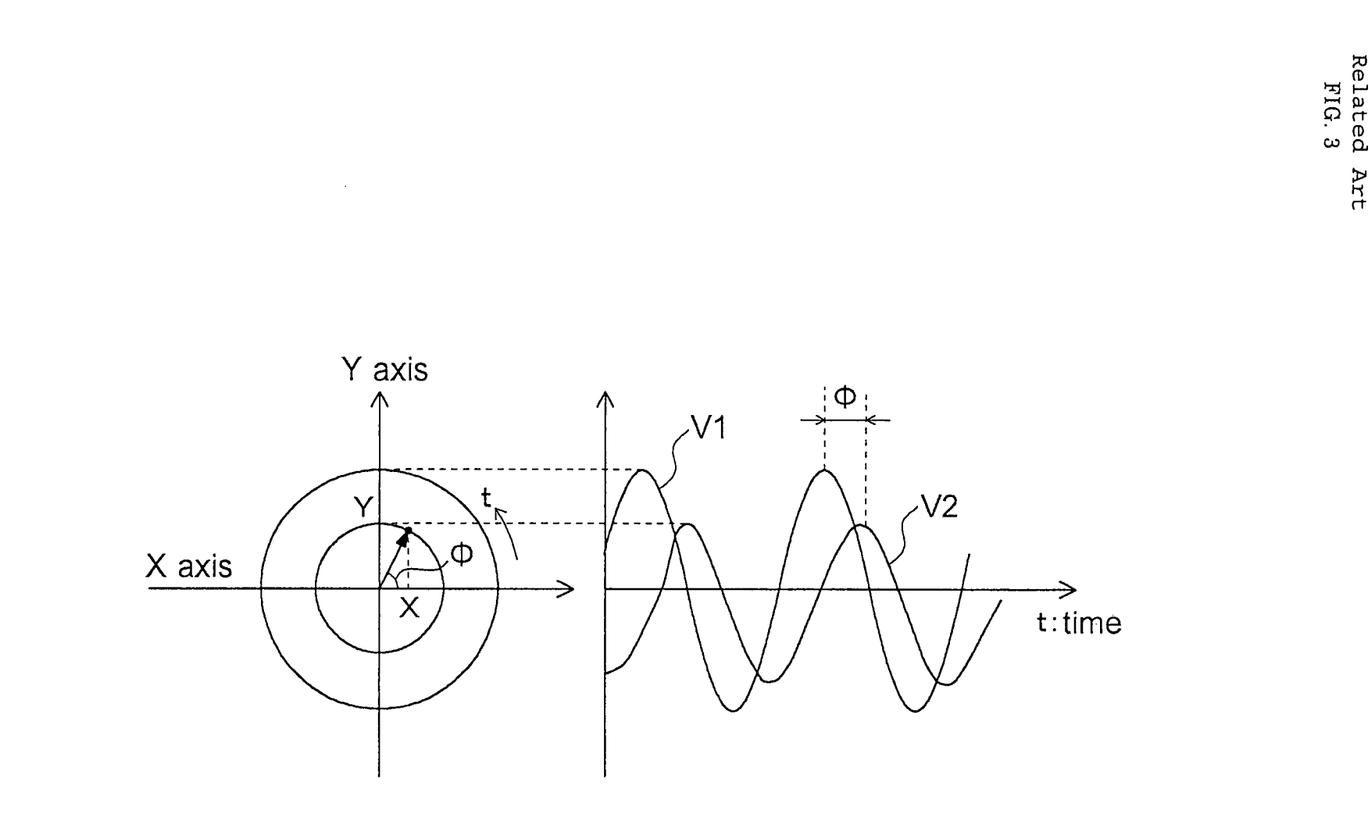
FIG. 3 shows a relationship between an AC excitation signal and a detection signal.

The detection signal V2 detected by the detection coil 8 reflects the permeability in the portion 6a (workpiece 6). If the permeability of the portion 6a is high, the magnetic flux accompanied with the generation of the eddy current is high, so that the detection signal V2 is large. If the permeability of the portion 6a is low, the magnetic flux is low, and therefore the detection signal V2 is small. To quantify the detection signal V2 based on the eddy current, as shown in FIG. 3, the amplitude value Y and the value X derived from the phase difference Φ (=Y cos Φ) are focused, and the following knowledge is available.

First, the amplitude value Y of the detection signal V2 has a relationship with the hardness of the hardened surface. As known from the relationship between the curves 4 and 5 in FIG. 1, there is a relationship that if the hardness of the surface is low, the permeability is high. If the permeability is high, the magnetic flux generated when the AC excitation signal V1 is applied to the exciting coil 7 is strong, and therefore the eddy current induced on the surface of the portion 6a is strong. Thus, the amplitude value Y of the detection signal V2 detected by the detection coil 8 is large. Vice versa, the amplitude value Y of the detection signal V2 detected by the detection coil 8 leads the magnetic flux penetrating the portion 6a where the eddy current occurs, that is the permeability. As the result, the relationship between the curves 4 and 5 shown in FIG. 1 leads the hardness of the hardened surface.

Second, the value X defined by the phase difference Φ of the detection signal V2 with respect to the AC excitation signal V1 has a relationship with the hardening depth (depth of the hardened layer). If the hardening depth is large, that is the hardened layer 1 is thickened, the area having low permeability is extended in the depth direction, and the phase delay of the detection signal V2 with respect to the AC excitation signal V1 is increased. As the result, the value derived from the phase difference Φ leads the hardening depth.

In the eddy current measurement for inspection of the hardening quality of the hardened member using the measurement principle described above, the eddy current measuring sensor with the exciting coils and the detection coils is used. Hereinafter, the structure of the eddy current measuring sensor is described in detail.

[First Embodiment]

FIGS. 4 to 7 depict the first embodiment of the eddy current measuring sensor according to the invention.

Figure 4:
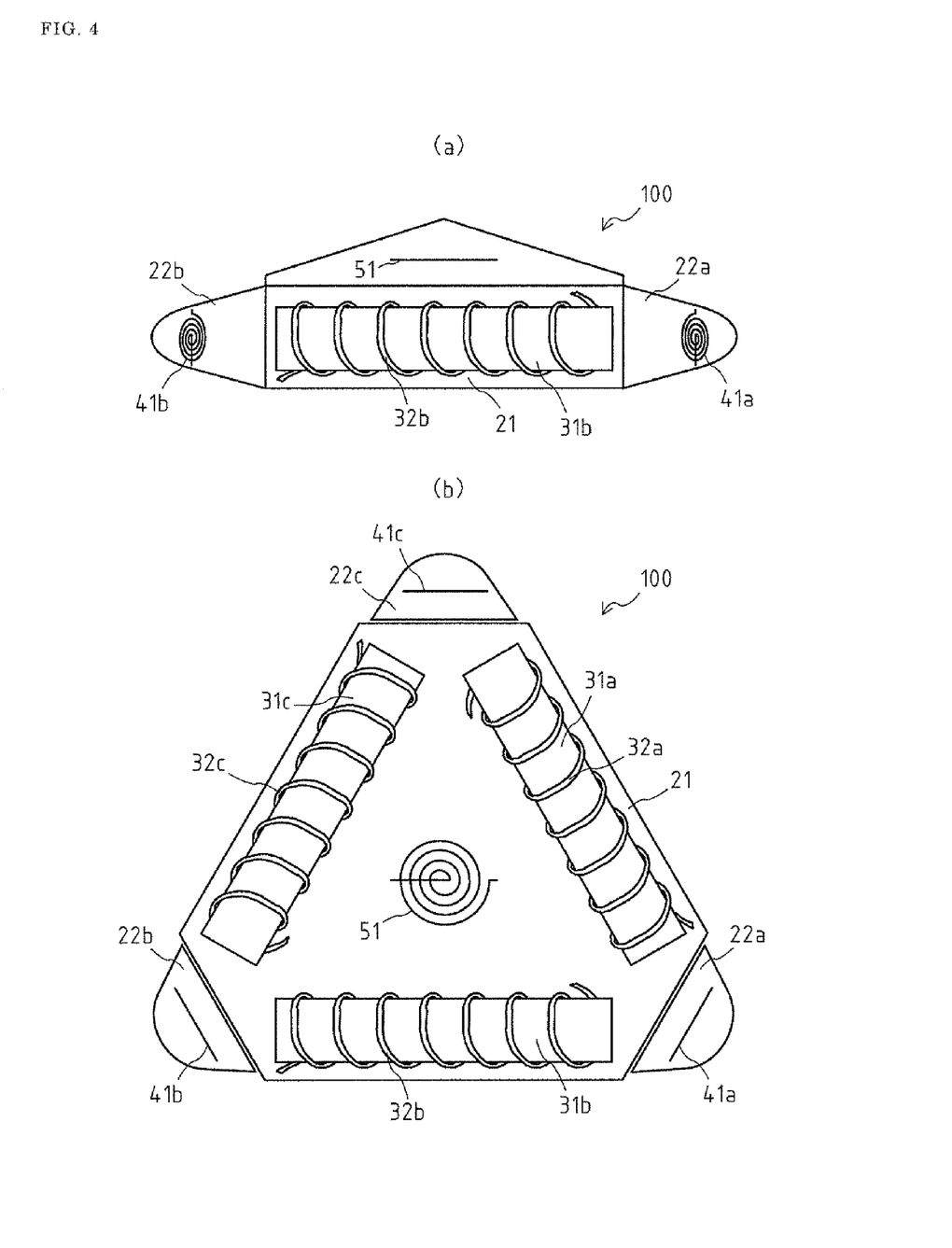
FIG. 4 depicts an eddy current measuring sensor in accordance with First embodiment, (a) is a front view, (b) is a plan view.

The sensor includes a probe 100 configured in regular triangle with an excitation unit and a detection unit as shown in FIG. 4. The excitation unit applies the alternating current excitation signal (referred as the AC excitation signal V1) to the workpiece. The detection unit detects the detection signal (referred as the detection signal V2) caused by the eddy currents generated on the workpiece.

In the description, as to the probe 100, the upper side, the lower side, the left side and the right side are defined as in FIG. 4(*a*), and the front side is defined as the front side of the plane and the back side is defined as the back side of the plane.

The probe 100 is arranged at the end of a rod (not shown) of the sensor that is extended toward the workpiece. The rod is slidable in the axis direction of the sensor. The probe 100 is configured such that the distance between the probe and the workpiece is changeable (see FIG. 7(*a*)). Moreover, the probe 100 can be rotatable around the axis of the sensor so that the attitude of the probe 100 toward the workpiece (see FIG. 7(*b*)).

Figure 6:
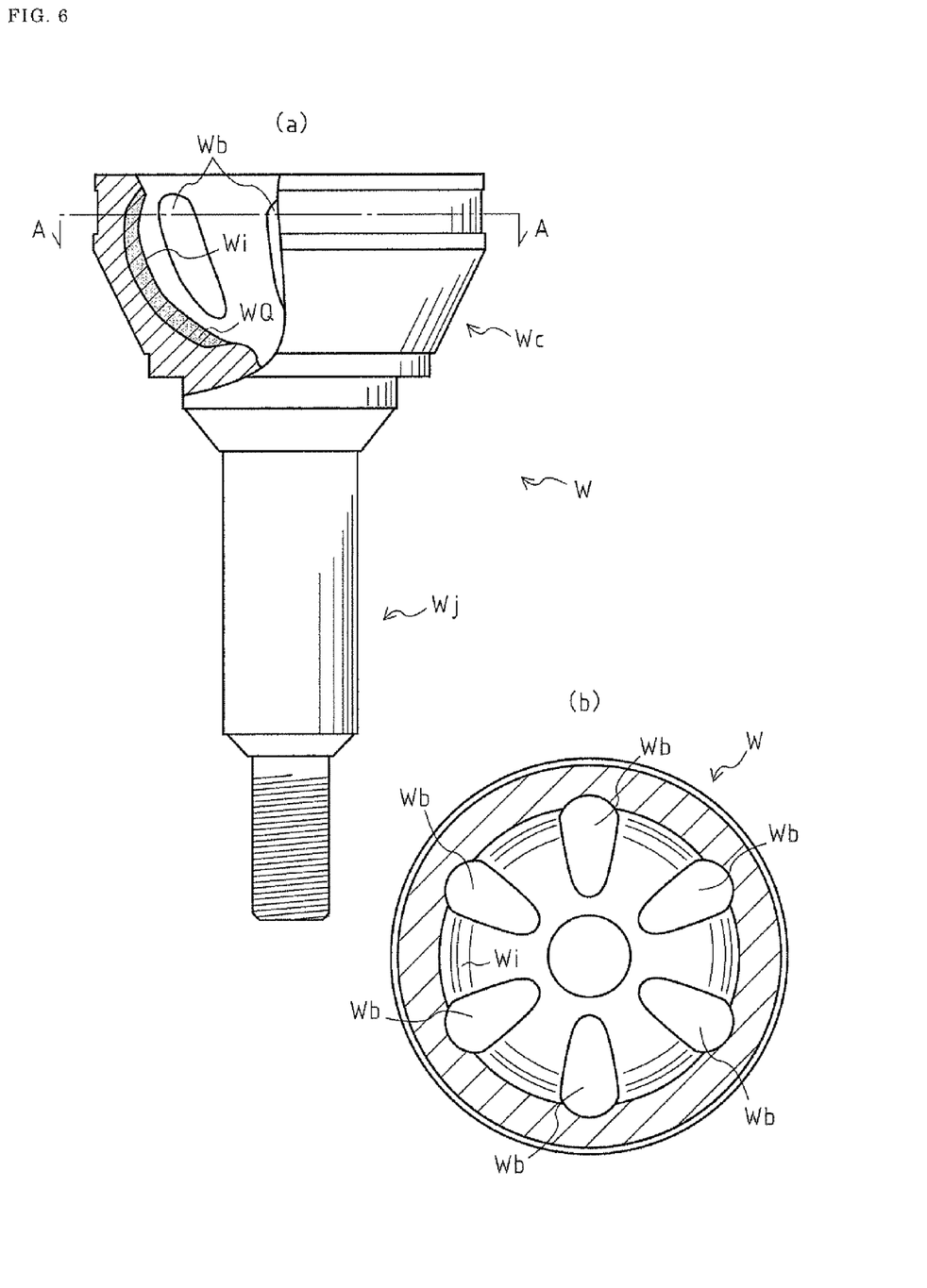
FIG. 6 illustrates a CVJ outer race as the object, (a) is a partially cutaway side view, (b) is a cross section along A-A line.
Figure 7:
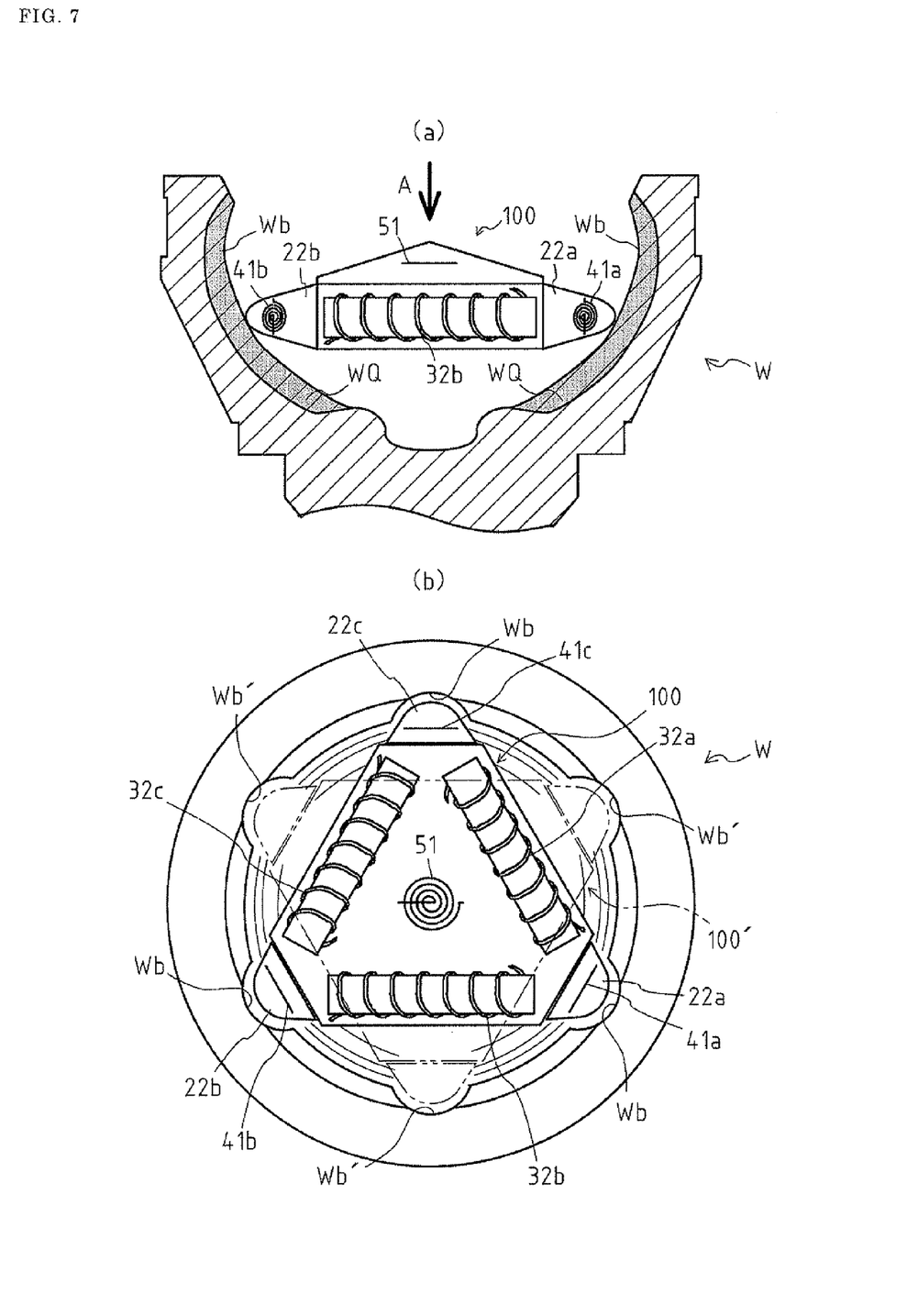
FIG. 7 depicts a measurement situation using the sensor, (a) is a cross-section, (b) is a plan view.

In the embodiment, as shown in FIGS. 6(*b*) and 7(*b*), the workpiece is a CVJ outer race with six ball grooves, so that the best shape of the probe 100 is regular triangle as shown in FIG. 4(*b*). The shape of the probe 100 is not limited to the regular triangle, but it may be the regular polygon (square and the like). More specifically, the shape is selectable in accordance with the shape of the workpiece.

The excitation unit includes a first exciting coil 32a, a second exciting coil 32b and a third exciting coil 32c, each of which is arranged on a side of the probe 100 and is configured as a solenoid coil.

In detail, as shown in FIG. 4(*b*), the probe 100 has a case 21 formed with substantially regular triangle (or hexagon) shape, along the three sides of which a first core 31a, a second core 31b and a third core 31c are respectively arranged. The cores 31a to 31c are made of magnetic materials having high magnetic permeability such as ferrite or permalloy and surrounded by the coils 32a to 32c, respectively. Each of the coils 32a to 32c is connected to an alternating current source (not shown). As described, the coils 32a to 32c are the exciting coils to apply the AC excitation signal to the workpiece, and the cores 31a to 31c are to heighten the magnetic fields generated by the coils 32a to 32c.

The detection unit includes a first detection coil 41a, a second detection coil 41b and a third detection coil 41c, each of which is arranged at a vertex of the probe 100 and is configured as a pancake coil.

In detail, as shown in FIG. 4(*b*), the probe has a first coil case 22a, a second coil case 22b and a third coil case 22c, each of which is arranged at the vertex of the case 21. The coil cases 22a to 22c contain the detection coils 41a to 41c, respectively. Each of the detection coils 41a to 41c is connected to a measurement instrument (not shown). Thus, the detection coils 41a to 41c detect the detection signal in response to the eddy currents generated in the workpiece to which the AC excitation signal is applied.

In the embodiment, in order to detect and evaluate the magnetic fields generated in the perpendicular direction and in the horizontal direction with the same sensitivity, the detection coils 41a to 41c are both configured in the pancake coils, but a plane coil or a solenoid coil can be substituted for the pancake coil. In the case where the magnetic field in the perpendicular direction is the main target of detection and evaluation, the solenoid coil arranged in the perpendicular direction can be substituted for the pancake coil. In the case where the magnetic field in the horizontal direction is the main target of detection and evaluation, the solenoid coil arranged in the horizontal direction can be substituted for the pancake coil. In the alternative embodiment, the hole devices can be applicable as the detection coils.

The detection unit further includes a balance coil 51 arranged at the center of the probe 100.

In detail, as shown in FIG. 4(*b*), the balance coil 51 is arranged in the case 21 where the distance from each of the detection coils 41a to 41c is substantially same. The balance coil 51 is connected to the measurement instrument such that the electromotive forces generated by the detection coils 41a to 41c are cancelled each other. The arrangement of the balance coil 51 and the detection coils 41a to 41c can decrease influence of disturbance on the probe 100 such as temperature. It should be noticed that the probe can be configured without the balance coil 51, however, the balance coil 51 is preferably installed in the detection unit so as to reduce the influence of disturbance.

To measure the eddy current using the eddy current sensor, the probe 100 is kept in the proximity of the workpiece, and the alternating current is applied to at least one of the exciting coils 32a to 32c as the AC excitation signal. The magnetic field is generated in the position facing one of the detection coils 41a to 41c, and therefore the eddy current is occurred in response to the magnetic field. The eddy current can be detected by at least one of the detection coil 41a to 41c, thereby measuring the eddy current in the workpiece on the basis of the detection signal.

Figure 5:
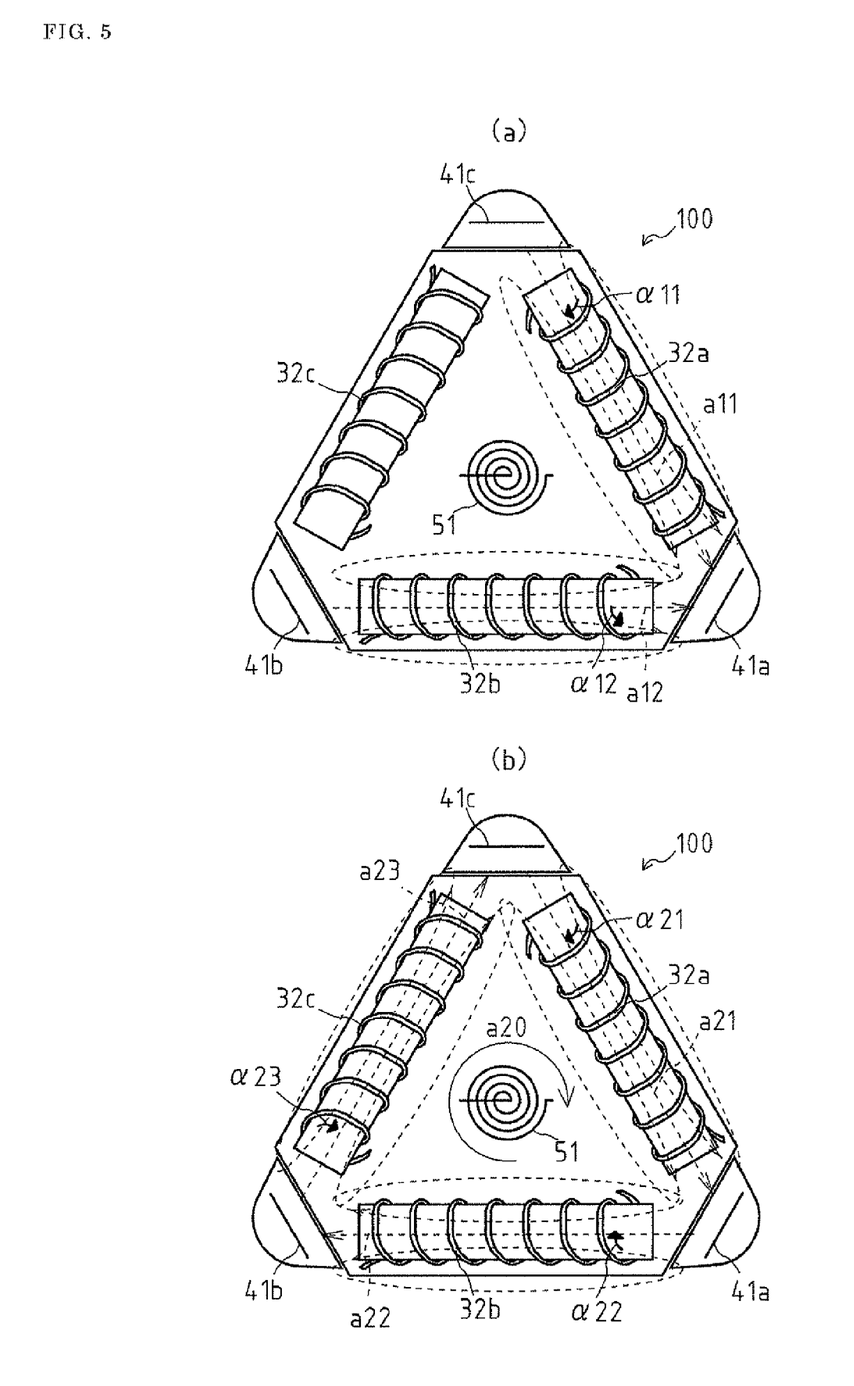
FIG. 5 depicts magnetic fields generated in measuring the eddy current using the sensor, (a) shows a first example, (b) shows a second example.

FIG. 5(a) shows a first example of the method of eddy current inspection with the eddy current measuring sensor. As shown in FIG. 5(a), in the measuring method, the strong magnetic field is generated at the position of the workpiece corresponding to the position where one of the detection coils is located, to which the magnetic fields to be generated by the exciting coils are gathered.

In this example, the alternating current source applies the voltage to the first and second exciting coils 32a and 32b. The timings of applying the voltage to the coils 32a and 32b are controlled such that the magnetic field generated in the coil 32a is oriented to the detection coil 41a and the magnetic field generated in the coil 32b is oriented to the detection coil 41a.

As depicted in FIG. 5(a), when the current flows along Arrow α11 in the coil 32a, due to Ampère's circuital law, the magnetic field is produced along Arrow a11 in the coil 32a. When the current flows along Arrow α12 in the coil 32b, the magnetic field is produced along Arrow a12 in the coil 32b. The magnetic fields produced by the coils 32a and 32b are directed at the detection coil 41a.

The magnetic fields lead the electromagnetic induction, which generates the eddy currents in the workpiece (magnetic body). Due to the eddy currents on the surface of the workpiece, the magnetic flux penetrates the detection coil 41a, thereby generating the inductive voltage in the detection coil 41a. Thus, the detection coil 41a can measure the inductive voltage.

The magnetic fields produced in the coils 32a and 32b are directed at the position of the workpiece facing the detection coil 41a, so that the strong magnetic field and the eddy currents can be generated. The exciting coils to which the alternating current is applied are switched in order (e.g., clockwise in plan view), and the detection coil that measures the inductive voltage (the detection coil to which the magnetic fields produced in the exciting coils are oriented) is switched in order, and thus the measurement is performed. For instance, applying the alternating current to the exciting coils 32a and 32b and measuring the inductive voltage by the detection coil 41a, applying the alternating current to the exciting coils 32b and 32c and measuring the inductive voltage by the detection coil 41b, and applying the alternating current to the exciting coils 32c and 32a and measuring the inductive voltage by the detection coil 41c, the measurement is performed by switching the exciting coils 32a, 32b and 32c and the detection coils 41a, 41b and 41c.

As described above, each of the detection coils 41a to 41c disposed in the vertexes of the probe 100 can measure the eddy current.

FIG. 5(b) depicts a second example of the method of eddy current inspection with the eddy current measuring sensor. As shown in FIG. 5(b), the magnetic fields are generated at the positions facing the detection coils 41a to 41c, thereby producing the eddy current.

In this example, the alternating current source applies the voltage to the exciting coils 32a to 32c. The timing of applying the voltage is controlled such that the magnetic field produced in the first exciting coil 32a is oriented clockwise around the center of the probe 100, and the magnetic field produced by the second and third exciting coils 32b and 32c are oriented clockwise.

As depicted in FIG. 5(b), when the current flows along Arrow α21, due to the Ampère's circuital law, the magnetic field is produced along Arrow a21 in the coil 32a. When the currents flow along Arrows α22 and α23, the magnetic fields are produced along Arrows a22 and a23 in the coils 32b and 32c, respectively. Three magnetic fields are generated in three coils 32a to 32c in the clockwise direction at the same time. Therefore, at the center of the probe 100, the rotating magnetic field a20 is produced as shown in FIG. 5(b).

The magnetic fields lead the electromagnetic induction, which generates the eddy currents in the workpiece (magnetic body). Due to the eddy currents on the surface of the workpiece, the magnetic flux penetrates the detection coils 41a to 41c, thereby generating the inductive voltage in the detection coils 41a to 41c. Thus, the detection coils 41a to 41c can measure the inductive voltage.

In this example, the magnetic fields generated in the coils 32a to 32c are produced at the positions of the workpiece facing the detection coils 41a to 41c, so that eddy currents can be generated and measured. Thus, the detection coils 41a to 41c disposed at the vertexes of the probe 100 can measure the eddy currents at the same time.

As described above, the eddy current measuring sensor can control the voltage applied to the exciting coils 32a to 32c to change the existence or the orientation of the magnetic field generated in the exciting coils 32a to 32c. As a result, the pattern of the eddy currents, which are produced at the position facing the detection coils 41a to 41c, is changeable according to the measurement situation.

FIG. 6 illustrates a CVJ outer race W as the object to be measured with the eddy current measuring sensor.

As depicted in FIG. 6, the CVJ outer race W is a part of a constant velocity joint (CVJ) that is one of the ball joints.

The CVJ outer race W has a cup portion Wc and a joint portion Wj.

The cup portion Wc has an opening at one end (upper end in FIG. 6(a)), into which a CVJ inner race and multiple balls (both not shown) are inserted. The inside Wi of the cup portion Wc is formed with six ball grooves Wb that are extended from the open end to the bottom side (bottom side of the cup portion Wc). The ball grooves Wb are arranged in the circumferential direction of the inside Wi at regular intervals, into each of which a ball (not shown) is fitted.

The joint portion Wj has a column shape projected in the direction opposite to the opening of the cup portion Wc. The joint portion has a male thread at the end to which the drive shaft or the like is fixed.

CVJ outer race W is required to have high dimensional accuracy and wear resistance in order to transmit the driving force with high efficiency for the long term. To answer the requirement, the surfaces of the inside Wi and the ball grooves Wb are quenched. In the drawings, the quenched portion (hardened layer) WQ is shown with shade.

FIG. 7 shows the way to use the eddy current measuring sensor to perform the eddy current inspection for the CVJ outer race W. In the description, the measurement points are set in the ball grooves Wb, which have high difficulty due to the complex shape.

In the eddy current inspection using the sensor to inspect the ball grooves Wb of the CVJ outer race W, the probe 100 is arranged to face the opening of the cup portion Wc of the CVJ outer race W. The rod is extended toward the workpiece as Arrow A in FIG. 7, thereby inserting the probe 100 into the cup portion Wc. As depicted in FIG. 7, the coil cases 22a to 22c are placed in contact with the three ball grooves Wb alternately. In other words, the probe 100 is arranged in the proximity of the CVJ outer race W and the coil cases 22a to 22c meet the ball grooves Wb.

In such state, as described above, the alternating voltage is applied to at least one of the exciting coils 32a to 32c as the AC excitation signal. Thus, the magnetic field is produced at the position corresponding to at least one of the detection coils 41a to 41c, and the magnetic field generates the eddy current in the workpiece. At least one of the detection coils 41a to 41c detect the inductive voltage caused by the eddy current as the detection signal, whereby the eddy current inspection for the CVJ outer race W is performed on the basis of the detection signal.

After that, the rod is shortened toward the base side to be removed from the inside of the cup portion Wc, and the probe 100 is rotated by 180° around the axis perpendicular to the CVJ outer race W (to the opening face of the cup portion Wc). The probe 100 is inserted into the cup portion Wc again, and the coil cases 22a to 22c are placed in contact with the ball grooves Wb' as shown in two-dot chain line in FIG. 7(b). In the state, the eddy current inspection is performed.

The sensor in accordance with the embodiment has the probe 100 configured in regular triangle, so that the coil cases 22a to 22c can be placed in touch with three ball grooves Wb of the CVJ outer race W and three-point positioning can be carried out. Due to the structure, the probe 100 can be positioned with high accuracy and repeatability with respect to the workpiece.

The eddy current measuring sensor can inspect the steel materials having the complex inside shape in which the hardening is performed three-dimensionally. For example, if the object is the CVJ outer race W, the eddy current inspection using the probe 100 can be provided with high stability and repeatability regarding the positioning thereof.

Moreover, the CVJ outer race W has six ball grooves Wb. In this case, the probe 100 with regular triangle shape can perform the eddy current inspection to the entire ball grooves Wb by two step measurements in which the probe 100 is rotated by 180°. The probe 100 is inserted into the cup portion Wc twice, and thus all ball grooves Wb are inspected, thereby shortening the measurement time.

As described before, the shape of the probe 100 may be the regular polygon other than the triangle according to the shape of the workpiece. For instance, in the case that the CVJ outer race W has eight ball grooves Wb, the probe 100 can have square shape.

[Second Embodiment]

Figure 8:
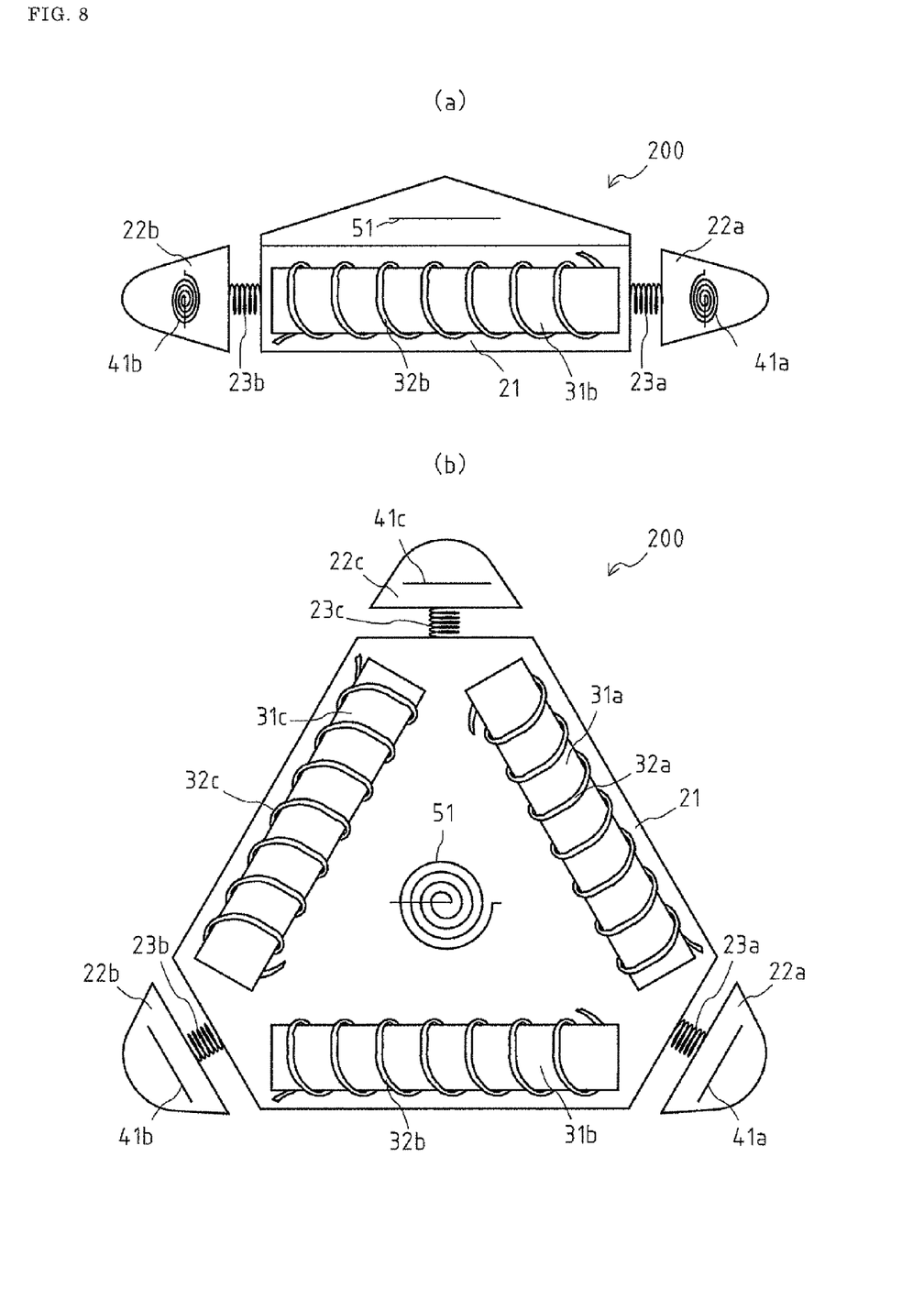
FIG. 8 depicts an eddy current measuring sensor in accordance with Second embodiment, (a) is a front view, (b) is a plan view.
Figure 9:
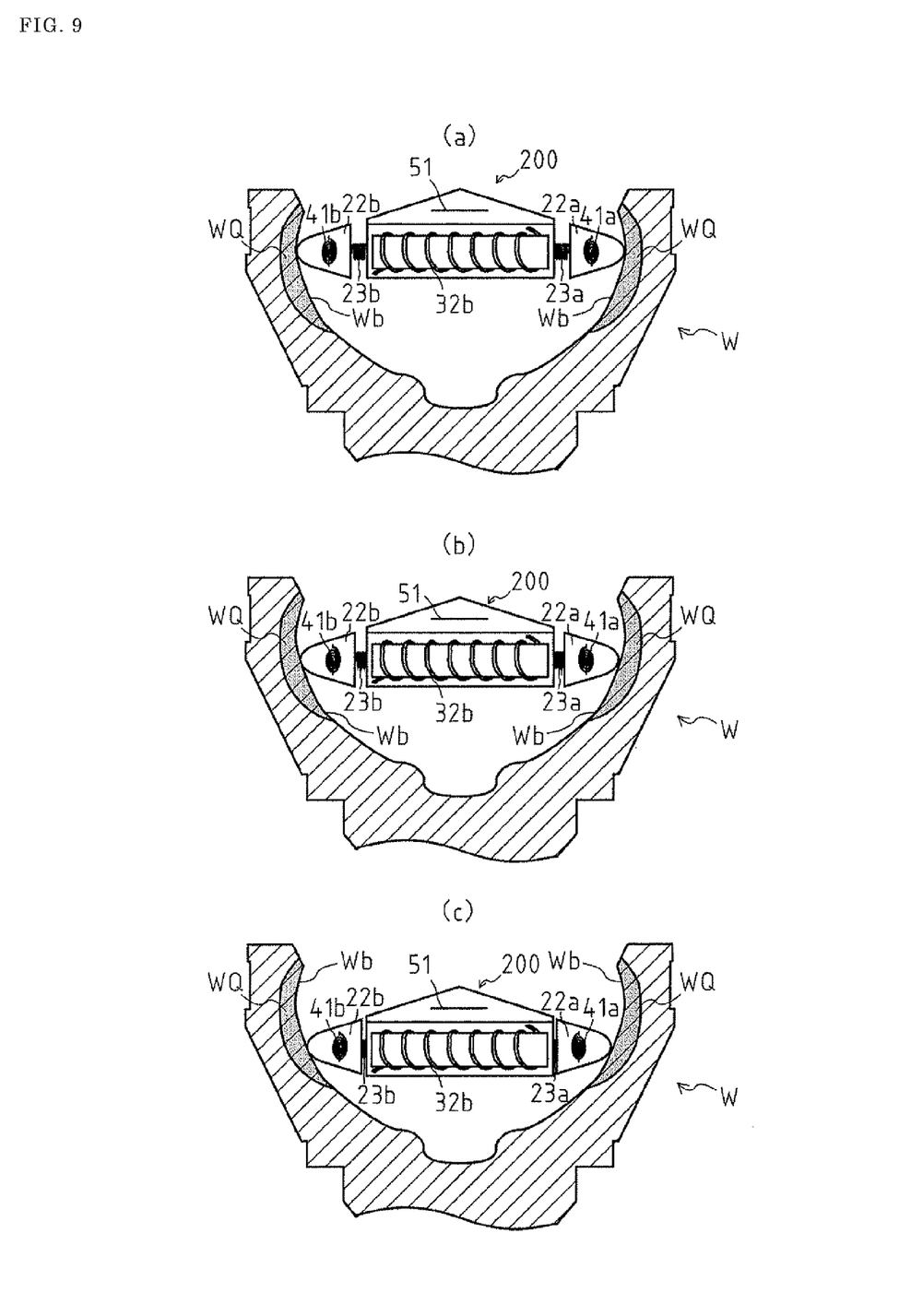
FIG. 9 illustrates measurement situations using the sensor in order: from (a) to (c).
Figure 10:
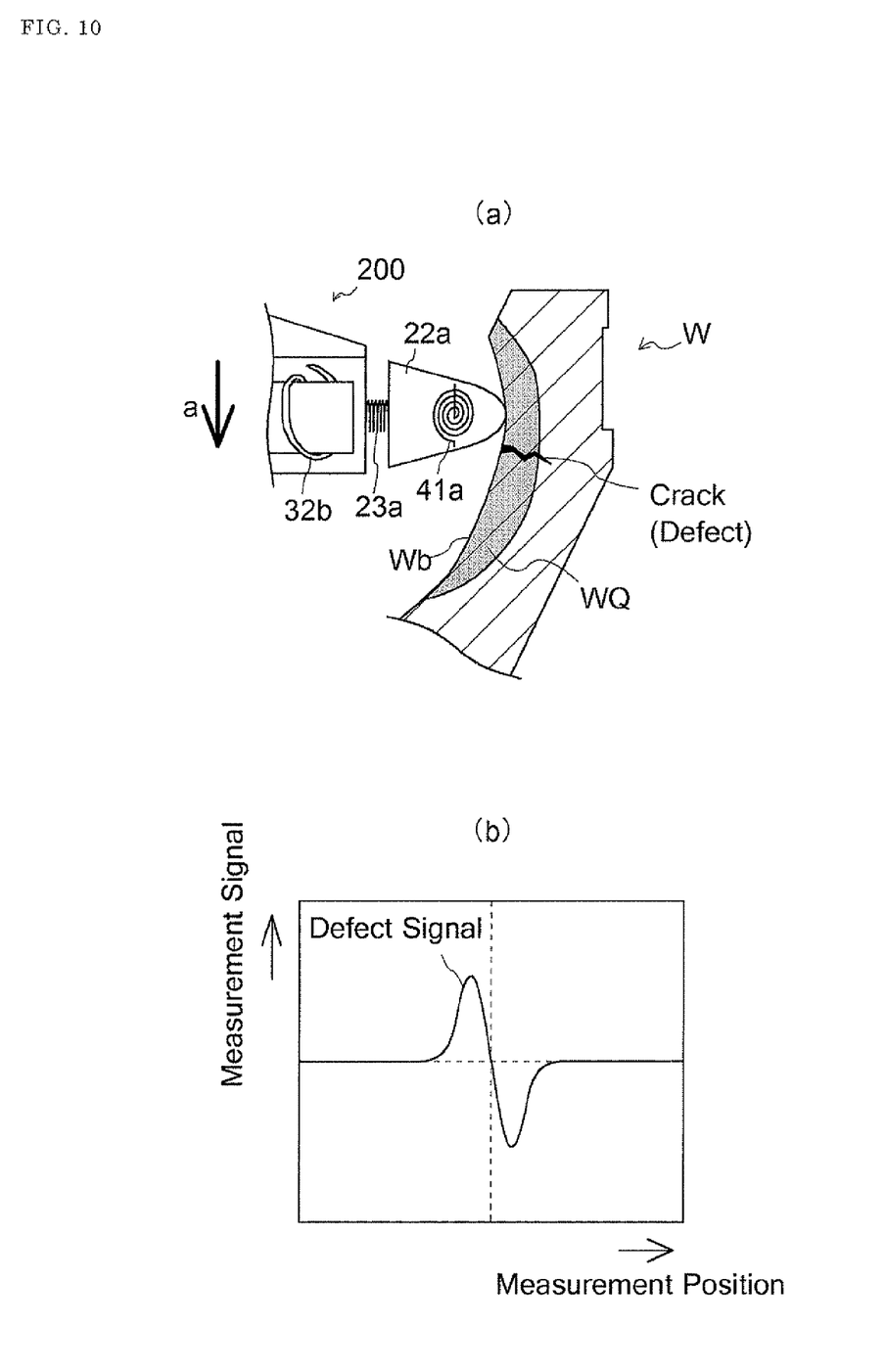
FIG. 10 shows the measurement situation in detail, (a) is an enlarged cross section, (b) shows the measurement result.

FIGS. 8 to 10 depict the second embodiment of the eddy current measuring sensor according to the invention. In the following description, the identical or corresponding members described above are marked with the same reference signs and a detailed description thereof is omitted.

As shown in FIG. 8(a), the eddy current measuring sensor according to this embodiment includes a probe 200 having the excitation unit and the detection unit as First embodiment. The excitation unit includes the excitation coils 32a to 32c configured in the solenoid coils, disposed at the sides of the probe 200. The detection unit includes the detection coils 41a to 41c configured in the pancake coils, disposed at the vertexes of the probe 200, and the balance coil 51 disposed at the center of the probe 200.

In this embodiment, the detection coils 41a to 41c are extendable toward outside from the vertexes of the probe 200.

As shown in FIG. 8(b), at the corners of the case 21 (the vertexes of the probe 200), the first coil case 22a, the second coil case 22b and the third coil case 22c are arranged via a first spring 23a, a second spring 23b and a third spring 23c. The detection coils 41a to 41c are installed in the coil cases 22a to 22c.

In this embodiment, the detection coils 41a to 41c are arranged via the springs 23a to 23c at the vertexes of the probe 200, but the detection coils 41a to 41c may be extendable outward by means of alternative structures. For instance, the actuators such as motorized cylinders can be arranged to the vertexes of the probe 200, to which the detection coils 41a to 41c are attached. From the viewpoint of lowering production costs and improving simplicity, the springs are advantageous to set the detection coils 41a to 41c.

FIG. 9 depicts the method of measuring the eddy current for the CVJ outer race W with the eddy current measuring sensor.

In the eddy current inspection using the sensor to inspect the ball grooves Wb of the CVJ outer race W, the probe 200 is arranged to face the opening of the cup portion Wc. As shown in FIG. 9(a), the coil cases 22a to 22c are placed in contact with the three ball grooves Wb. The springs 23a to 23e are compressed a little. The coil cases 22a to 22c are biased outward by the elastic force of the springs 23a to 23c, whereby the coil cases are pressed to the ball grooves Wb.

In such state, as First embodiment, the alternating voltage is applied to at least one of the exciting coils 32a to 32c as the AC excitation signal, starting the eddy current inspection to the CVJ outer race W.

Continuing the inspection, the rod is extended, and the probe 200 moves the bottom side of the cup portion Wc. At this time, the springs 23a to 23c are compressed according to the shape of the cup portion Wc (of the ball grooves Wb). The inner diameter of the inside Wi is gradually decreased in accordance with the depth of the cup portion Wc, the coil cases 22a to 22c are pressed inward by the ball grooves Wb, thereby increasing the compression amount of the springs 23a to 23c. If the probe 200 goes to the bottom side of the cup portion Wc, the biasing forces added to the coil cases 22a to 22c by the springs 23a to 23c become stronger, thereby the probe 200 is kept in contact with the ball grooves Wb.

As shown in FIGS. 9(b) and FIGS. 9(c), the probe 200 is stopped at the measurement points to obtain the measurement value. Using the standard curve made based on the measurement results, the measurement values can be set up as hardening depth (the thickness of the hardened layer WQ from the surface). Connecting the dots in accordance with the hardening depth at the measurement points, as shown in FIG. 9, the three-dimensional hardening shape of the CVJ outer race W can be obtained.

As First embodiment, the probe 200 is rotated by 180° around the axis perpendicular to the CVJ outer race W, and the eddy current inspection is performed to the ball grooves Wb'.

In the eddy current measuring sensor of this embodiment, the detection coils 41a to 41c are extendable outward from the vertexes of the probe 200, so that the eddy current inspection can be applicable to the object having the varying inner diameter. In detail, the continuous eddy current inspection can be applicable to the CVJ outer race W having the varying shape in the ball grooves Wb. That is, the hardening shape of the CVJ outer race W is visualized three-dimensionally by a non-destructive inspection.

The sensor according to the second embodiment may be used for an inspection to detect cracks caused by hardening.

During the eddy current inspection, the probe 200 moves along Arrow a in FIG. 10(a) toward the bottom side of the cup portion Wc. The alternating voltage is applied to at least one of the exciting coils 32a to 32c as the AC excitation signal, and the coil cases 22a to 22c are slid along the ball grooves Wb. At this time, if the probe crosses the crack (defect) as depicted in FIG. 10(a), the measurement signal varies significantly as shown in FIG. 10(b), so that the defect signal can be detected. As a result, the sensor according to the second embodiment can find the hardening cracks occurred in the CVJ outer race W.

[Third Embodiment]

Figure 11:
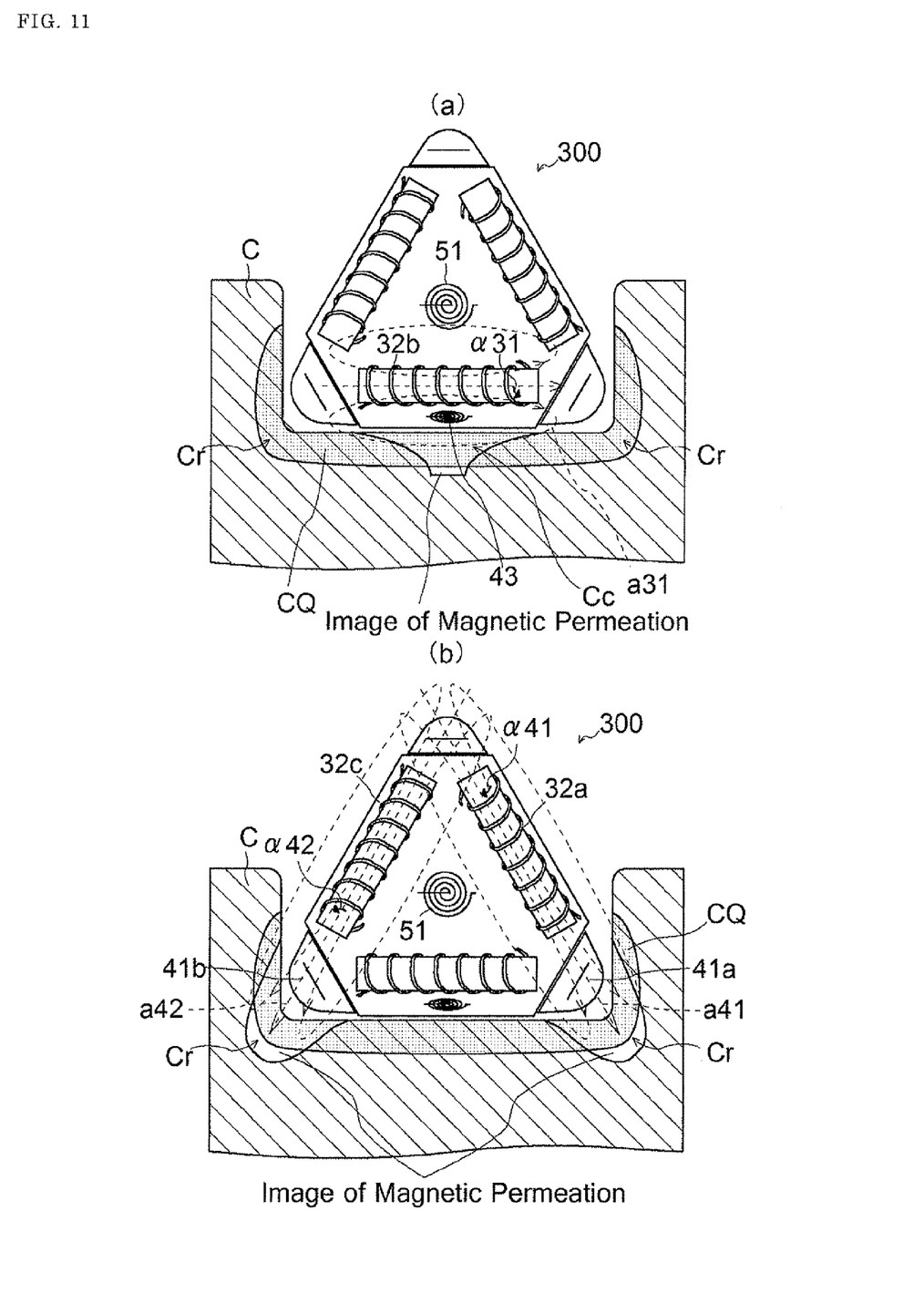
FIG. 11 depicts measurement situations using an eddy current measuring sensor in accordance with Third embodiment, (a) shows a first example, (b) shows a second example.

FIG. 11 depicts the third embodiment of the eddy current measuring sensor according to the invention.

As depicted in FIG. 11, the eddy current measuring sensor according to this embodiment includes a probe 300 having the excitation unit and the detection unit as First embodiment. The excitation unit includes the excitation coils 32a to 32c configured in the solenoid coils, disposed at the sides of the probe 300. The detection unit includes the detection coils 41a to 41c configured in the pancake coils, disposed at the vertexes of the probe 300, and the balance coil 51 disposed at the center of the probe 300.

The detection unit further includes a forth detection coil 43 disposed at the side of the probe 300, configured as the pancake coil. As shown in FIG. 11(a), the forth detection coil 43 is arranged at the center of the second exciting coil 32b and outer side than the coil 32b. The forth detection coil 43 is connected to the measurement instrument and detects the detection signal generated by the eddy currents in the workpiece to which the AC excitation signal. The forth detection coil 43 may be installed in all sides of the probe 300. The forth coil 43 can be configured as a plane coil, a solenoid coil or hole device in place of the pancake coil.

FIG. 11 shows the embodiment, in which the hardening depth of a crank shaft C is measured with the eddy current measuring sensor. In this embodiment, the measurement object is a journal portion of the crank shaft C, in which the center portion Cc and the corner portions Cr have quenched portion (hardened layer) CQ. The sensor can be applicable to a pin portion of the crank shaft C, a cam shaft and the like.

FIG. 11(a) shows a first example of the method of measuring the hardening depth of the center portion Cc of the crank shaft C.

In this example, as shown in FIG. 11(a), the probe 300 is arranged such that the forth detection coil 43 faces the center portion Cc of the journal portion.

The excitation voltage is applied to the second exciting coil 32b as the AC excitation signal so that the magnetic field is produced at the center portion Cc of the journal portion and the eddy currents occur due to the magnetic field. As depicted in FIG. 11(a), when the current flows along Arrow α31 in the coil 32b, due to the Ampère's circuital law, the magnetic field is produced along Arrow a31 in the coil 32b. The forth detection coil 43 detects the inductive voltage generated by the eddy currents as the detection signal, thereby inspecting the quenched portion CQ at the center portion Cc of the journal portion on the basis of the detection signal.

FIG. 11(b) shows a second example of the method of measuring the hardening depth of the corner portions Cr.

In this example, as shown in FIG. 11(b), the probe 300 is arranged such that the first and second detection coils 41a and 41b face the corner portions Cr of the journal portion.

The excitation voltage is applied to the first and third exciting coils 32a and 32c as the AC excitation signal so that the magnetic fields are produced at the corner portions Cr of the journal portion and the eddy currents occur due to the magnetic fields. As depicted in FIG. 11(b), when the currents flow along Arrows α41 and α42 in the coils 32a and 32c, due to the Ampère's circuital law, the magnetic fields are produced along Arrows a41 and a42 in the coils 32a and 32c. The detection coils 41a and 41b detect the inductive voltages generated by the eddy currents as the detection signal, thereby inspecting the quenched portion CQ at the corner portions Cr of the journal portion on the basis of the detection signals.

As described above, the voltages applied to the exciting coils 32a to 32c is controlled in accordance with the shape of the journal portion of the crank shaft C, or the measurement points to be inspected. Therefore, the existence or direction of the magnetic field produced in the exciting coils 32a to 32c can be changed. In other words, the pattern of the eddy currents, which is produced at the quenched portion CQ of the journal portion, is changeable according to the measurement situation. In the case that the inspection object is the quenched portion CQ of the journal portion, the proper eddy currents can be produced in response to the center portion Cc and the corner portions Cr. That is, the particular portion selected from the quenched portion CQ can be detected by the hardening depth or hardness in the journal portion or the pin portion of the crank shaft C.

Industrial Applicability

The eddy current measuring sensor according to the invention is applicable to the eddy current inspection with high stability and repeatability with regard to positioning of the probe, in which the measurement object is the steel material having the complex inside shape to which the hardening is three-dimensionally performed.

The invention claimed is:

1. An eddy current measuring sensor comprising a probe configured in regular polygon, the probe comprising an excitation unit for applying a predetermined alternating current excitation signal to an object to be measured and a detection unit for detecting a detection signal generated in the object in response to the alternating current excitation signal, wherein the excitation unit comprises multiple exciting coils arranged along the each side of the probe, wherein the detection unit comprises multiple detection coils arranged at the each vertex of the probe, wherein locating the probe in the proximity of the object, an alternating voltage as the excitation signal is applied to at least one of the exciting coils, whereby a magnetic field is produced at a portion of the object facing the detection coil and an eddy current is generated by the magnetic field, wherein an inductive voltage generated by the eddy current is detected as the detection signal by means of at least one of the detection coils, whereby the eddy current measuring is performed on a basis of the detection signal, and the detection unit further comprises a balance coil arranged at the center of the probe for cancelling the electromotive forces generated by the detection coils.

2. The sensor according to claim 1, wherein
the detection coil is configured to be extendable outward from the vertex of the probe.

3. The sensor according to claim 2, wherein
the detection coil is arranged via an elastic member, whereby the detection coil is extendable outward.

4. The sensor according to claim 3, wherein
the detection unit further comprises a second detection coil arranged at least one side of the probe and arranged on an outer side of the exciting coil relative to the balance coil, locating the probe in the proximity of the object, an alternating voltage as the excitation signal is applied to at least one of the exciting coils, whereby a magnetic field is produced at a portion of the object facing the second detection coil and an eddy current is generated by the magnetic field, and an inductive voltage generated by the eddy current is detected as the detection signal by means of the second detection coil, whereby the eddy current measuring is performed on the basis of the detection signal detected by the second detection coil.

5. The sensor according to claim 2, wherein
the detection unit further comprises a second detection coil arranged at least one side of the probe and arranged on an outer side of the exciting coil relative to the balance coil,
locating the probe in the proximity of the object, an alternating voltage as the excitation signal is applied to at least one of the exciting coils, whereby a magnetic field is produced at a portion of the object facing the second detection coil and an eddy current is generated by the magnetic field, and
an inductive voltage generated by the eddy current is detected as the detection signal by means of the second detection coil, whereby the eddy current measuring is performed on the basis of the detection signal detected by the second detection coil.

6. The sensor according to claim 1, wherein
the detection unit further comprises a second detection coil arranged at least one side of the probe and arranged on an outer side of the exciting coil relative to the balance coil,
locating the probe in the proximity of the object, an alternating voltage as the excitation signal is applied to at least one of the exciting coils, whereby a magnetic field is produced at a portion of the object facing the second detection coil and an eddy current is generated by the magnetic field, and
an inductive voltage generated by the eddy current is detected as the detection signal by means of the second detection coil, whereby the eddy current measuring is performed on the basis of the detection signal detected by the second detection coil.

\* \* \* \* \*